US00PP11485P

United States Patent [19]

Zary

[11] Patent Number: Plant 11,485

[45] Date of Patent: Aug. 15, 2000

[54] FLORIBUNDA ROSE PLANT NAMED 'JACGRANT'

[75] Inventor: Keith W. Zary, Thousand Oaks, Calif.

[73] Assignee: Bear Creek Gardens, Inc., Medford, Oreg.

[21] Appl. No.: 09/216,342

[22] Filed: Dec. 18, 1998

[51] Int. Cl.[7] ..... A01H 5/00

[52] U.S. Cl. ..... Plt./147

[58] Field of Search ..... Plt./141, 146, 147, Plt./148

*Primary Examiner*—Howard J. Locker

*Attorney, Agent, or Firm*—Klarquist Sparkman Campbell Leigh & Whinston, LLP

[57] ABSTRACT

Floribunda rose plant having disease resistance; large, leathery foliage; and large, fragrant flowers of attractive orange-red color.

1 Drawing Sheet

The present invention relates to a new and distinct variety of rose plant of the floribunda class which was originated by me by crossing the variety 'JACdew' (U.S. Plant Pat. No. 5,122), with 'HARroony' (U.S. Plant Pat. No. 5,582).

The primary objective of this breeding was to produce a new rose variety having the disease resistance, vigorous growth and leathery foliage of the female parent combined with the fragrance and large flower size of the male parent. The objective was substantially achieved, along with other desirable improvements, as evidenced by the following unique combination of characteristics that are outstanding in the new variety and that distinguish it from its parents, as well as from all other varieties of which I am aware:

1. Large flowers;
2. Strong fragrance;
3. Attractive color in the flowers;
4. Large, leathery foliage; and
5. Good disease resistance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACdew', U.S. Plant Pat. No. 5,122.

*Pollen parent.*—'HARroony', U.S. Plant Pat. No. 5,582.

Classification:

*Botanical.*—*Rosa hybrida.*

*Commercial.*—Floribunda.

FLOWER

Observations made from specimens grown in a garden environment at Somis, Calif. from March 1996 to September 1998.

Blooming habit: Continuous.

Bud:

*Size.*—1½ inches long when the petals start to unfurl.

*Form.*—The bud form is long, pointed ovoid.

*Color.*—When sepals first divide, the bud color is Red Group 44C, but once sepals fully drop the color changes to Orange-Red Group 35C. When half blown, the upper sides of the petals are Orange-Red Group 35C with fading on petal edges to Orange Group 29D, and the lower sides of the petals are Orange-Red Group 35C.

*Sepals.*—Color: Green Group 138B often blushed with Red Group 46D when fully exposed to bright sun. Surface texture: Covered in fine hairs. There are three lightly appendaged sepals. There are two unappendaged sepals with hairy edges.

*Receptacle.*—Color: Green Group 137C. Shape: Funnel. Size: Medium (5/16" long×3/16" wide). Surface: Smooth.

*Peduncle.*—Length: Short (averaging about 2"). Surface: Smooth with a few glands. Color: Yellow-Green Group 146C. Strength: Stiff, erect.

Bloom:

*Size.*—Large. Average open size is 4 inches.

*Borne.*—Several together in clusters of three to five blooms having a rounded shape.

*Stems.*—Strength: Strong. Average lengths is 14–18 inches.

*Form.*—When first open: High centered. Permanence: Retains its form to the end. Outer petals curl back.

*Petalage.*—Number of petals under normal conditions: 30–35.

*Color.*—The upper sides of the petals are Orange-Red Group 35C with fading on the petal edges to Orange Group 29D. The reverse sides of the petals are Orange-Red Group 35C. The base of each petal has a small ¼"×¼" Yellow Group 4C half moon at the point of attachment. The major color on the upper sides in Orange-Red Group 35C.

*Variegations.*—None.

*Discoloration.*—At the end of the first day: No change. At the end of the third day: Some fading on petal edges to Orange Group 29D. by day five or six, the color continues to fade over ⅔ of the petal surface to Orange Group 29D.

*Fragrance.*—Strong, fruity.

Petals:

*Texture.*—Thick.

*Shape.*—Round.

*Form.*—Tips slightly recurved.

*Arrangement.*—Imbricated. Petaloids in the center: None.

*Persistence.*—Petals drop off cleanly before drying.

*Lastingness.*—On the plant: Long (about seven days). As a cut flower: Long (eight to nine days).

Reproductive parts:

*Anthers.*—Size: Medium. Quantity: Many. Color: Yellow. Arrangement: Regular around styles.

*Filaments.*—Color: Yellow.

*Pollen.*—Color: Gold.

*Styles.*—Color: Yellow.

*Stigmas.*—Color: Greenish-white.

Plant:

*Form.*—Bush.

*Growth.*—Vigorous; upright; branching; compact. At maturity, height is 3–3½ feet, and width is 2½ feet.

Foliage: Number of leaflets on normal mid-stem leaves: Five.

*Size.*—Large (6 to 6½" long×4 to 4½" wide.)

*Quantity.*—Abundant.

*Color.*—New foliage. Upper and lower surfaces: Greyed-Orange Group 176A. Old foliage: Upper Surface: Green Group 139A. Lower Surface: Green Group 139C.

*Shape.*—Pointed oval.

*Texture.*—Upper side: Leathery; glossy.

*Edge.*—Serrated.

*Serration.*—Single.

*Petiole rachis.*—Color: Green Group 138C.

*Petiole underside.*—Smooth with occasional prickles.

*Stipules.*—Long (¾"); serrated, bearded.

*Disease resistance.*—Susceptible to blackspot. Resistant to mildew and rust under normal growing conditions.

Wood:

*New wood.*—Color: Greyed-Orange Group 176A. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium; hooked slightly downward.

*Color when young.*—Greyed-Purple Group 183D.

*Color when mature.*—Greyed-Orange Group 164D.

Small prickles:

*Quantity.*—On main stalks: Many. On laterals: Few.

*Color.*—Greyed-Orange Group 164D.

I clam:

1. A new and distinct variety of rose plant of the floribunda class, substantially as herein shown and described, characterized particularly as to novelty by its disease resistance; large, leathery, foliage; and large, fragrant flowers of attractive orange-red color.

* * * * *

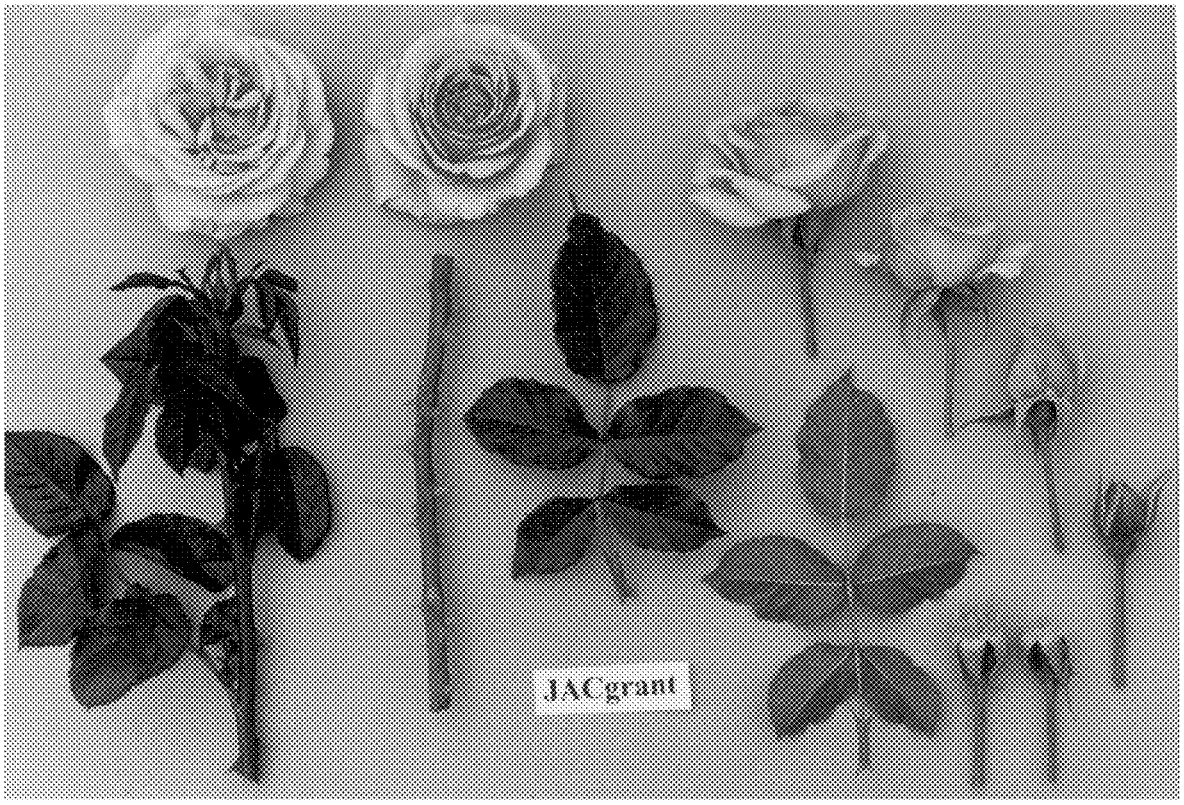
JACgrant